(12) United States Patent
Watson

(10) Patent No.: US 7,172,773 B2
(45) Date of Patent: Feb. 6, 2007

(54) FOOD SUPPLEMENT FORMULATION

(75) Inventor: Tommy Stanley Watson, Dunedin, FL (US)

(73) Assignee: Renew Life Inc., Clearwater, FL (US)

( * ) Notice: Subject to any disclaimer, the term of this patent is extended or adjusted under 35 U.S.C. 154(b) by 308 days.

(21) Appl. No.: 10/832,032

(22) Filed: Apr. 26, 2004

(65) Prior Publication Data
US 2005/0238636 A1 Oct. 27, 2005

(51) Int. Cl.
*A61K 36/53* (2006.01)
*A61K 38/46* (2006.01)
*A61K 35/60* (2006.01)

(52) U.S. Cl. .................. 424/747; 424/94.6; 424/523

(58) Field of Classification Search .................. None
See application file for complete search history.

(56) References Cited

U.S. PATENT DOCUMENTS

| 5,624,906 | A | * | 4/1997 | Vermeer ........................ 514/23 |
|---|---|---|---|---|
| 5,902,797 | A | * | 5/1999 | Bell et al. ..................... 514/54 |
| 5,968,896 | A | * | 10/1999 | Bell et al. ..................... 514/2 |
| 6,139,872 | A | * | 10/2000 | Walsh ......................... 424/464 |
| 6,228,368 | B1 | | 5/2001 | Gissmann et al. |
| 6,337,089 | B1 | * | 1/2002 | Yoshioka et al. ........... 424/451 |
| 6,365,176 | B1 | * | 4/2002 | Bell et al. ................... 424/439 |
| 6,743,770 | B2 | * | 6/2004 | Bell et al. ...................... 514/2 |
| 6,887,493 | B2 | * | 5/2005 | Shefer et al. ............... 424/490 |
| 2002/0044961 | A1 | * | 4/2002 | Kirschner et al. .......... 424/456 |
| 2003/0152629 | A1 | * | 8/2003 | Shefer et al. ............... 424/484 |
| 2005/0095208 | A1 | * | 5/2005 | Battaglia et al. ............. 424/48 |
| 2005/0186267 | A1 | * | 8/2005 | Thompson et al. ......... 424/451 |

OTHER PUBLICATIONS

Peirce, A. American Pharmaceutical Association—Practical Guide to Natural Medicines. 1999. pp. 498-499. Stonesong Press Book, William Mororrw and Company, Inc. New York, NY.*

* cited by examiner

*Primary Examiner*—Christopher R. Tate
(74) *Attorney, Agent, or Firm*—Fraser Martin & Miller LLC; Donald R. Fraser

(57) ABSTRACT

An improved food supplement formulation comprises fish oil, peppermint oil, and lipase.

12 Claims, No Drawings

FOOD SUPPLEMENT FORMULATION

FIELD OF THE INVENTION

The present invention relates generally to an improved food supplement formulation. More particularly, the invention is directed to a food supplement formulation containing essential fatty acids, which are important for maintaining good health.

BACKGROUND OF THE INVENTION

Natural compounds and herbal formulations can provide a supplement to the daily human diet. Certain compounds are useful to the human body, but are not produced in substantial quantities thereby. Thus, natural formulations have been found to be useful for supplementing the intake of these compounds from the human diet.

U.S. Pat. No. 6,228,368 discloses a food supplement formulation containing a mixture of fatty acids, including flaxseed oil and borage seed oil.

It would be desirable to prepare an improved food supplement formulation, which may be taken in excess of the daily human diet, which food supplement formulation may promote general health.

SUMMARY OF THE INVENTION

Accordant with the present invention, there surprisingly has been discovered an improved food supplement formulation, comprising fish oil, peppermint oil, and lipase.

The improved food supplement formulation according to the present invention is useful as a dietary supplement.

DETAILED DESCRIPTION OF THE PREFERRED EMBODIMENT

The present invention is directed to an improved food supplement formulation, comprising fish oil, peppermint oil, and lipase. The inventive formulation may be mixed together by conventional mixing equipment, and inserted, in dosage-sized quantities, into gelatin capsules for oral administration. Preferably, the inventive formulation is inserted into enteric-coated gelatin capsules.

Fish oil is a well-known compound, which contains high concentrations of eicosapentaenoic acid and docosahexaenoic acid. These polyunsaturated long-chain fatty acids have been shown to assist in preventing cardiovascular disease, by reducing triglycerides and cholesterol in the blood stream, thinning the blood, and increasing the high-density lipoprotines in the body.

Fish oil may be present in the inventive food supplement formulation at a concentration from about 80 to about 99 weight percent. Preferably, the concentration is from about 90 to about 98 weight percent. Most preferably, the concentration of fish oil is about 97.5 weight percent.

Peppermint oil is a well-known carminative herbal compound, known to be useful as a general digestive aid.

Peppermint oil may be present in the inventive formulation at a concentration from about 0.2 to about 4 weight percent. Preferably, the concentration is from about 0.5 to about 2 weight percent. Most preferably, the concentration of peppermint oil is about 1 weight percent.

Lipase is a well-known compound, consisting of enzymes that help the body's digestive system break down and digest fats, cellulose, carbohydrates, and proteins. Lipase enzymes are produced in the body's liver and pancreas. In a substantial number of people, however, the production of lipase enzymes is deficient. Lipase from plants may be used to supplement the body's production.

Lipase may be present in the inventive food supplement formulation at a concentration from about 0.3 to about 7 weight percent. Preferably, the concentration is from about 0.7 to about 3 weight percent. Most preferably, the concentration of lipase is about 1.5 weight percent.

The ingredients of the inventive food supplement formulation may synergistically work together to improve bodily functions such as, for example, cardiovascular function, joint flexibility, fat metabolism, nervous system and brain function, hormone production, cell division, and the relief of general digestive problems.

Conveniently, the inventive food supplement formulation may be taken orally at a dosage rate ranging from about 200 milligrams per day to about 4,000 milligrams per day. Preferably, the dosage rate is about 1,000 milligrams per day. The prescribed dosage rates may be effective to supplement the lack of important compounds required by the body for promoting general health.

This invention is more easily comprehended by reference to the specific embodiments recited hereinabove, which are representative of the invention. It must be understood, however, that the specific embodiments are provided only for the purpose of illustration, and that the invention may be practiced otherwise than as specifically illustrated without departing from its spirit and scope.

What is claimed is:

1. An improved food supplement formulation, comprising:
   from about 80 to about 99 weight percent fish oil;
   from about 0.2 to about 4 weight percent peppermint oil; and
   from about 0.3 to about 7 weight percent lipase.

2. The food supplement formulation according to claim 1, wherein the concentration of fish oil ranges from about 90 to about 98 weight percent.

3. The food supplement formulation according to claim 1, wherein the concentration of peppermint oil ranges from about 0.5 to about 2 weight percent.

4. The food supplement formulation according to claim 1, wherein the concentration of lipase ranges from about 0.7 to about 3 weight percent.

5. The food supplement formulation according to claim 1, wherein the concentration of fish oil is about 97.5 weight percent.

6. The food supplement formulation according to claim 1, wherein the concentration of peppermint oil is about 1 weight percent.

7. The food supplement formulation according to claim 1, wherein the concentration of lipase is about 1.5 weight percent.

8. An improved food supplement formulation, comprising:
   from about 90 to about 98 weight percent fish oil;
   from about 0.5 to about 2 weight percent peppermint oil; and
   from about 0.7 to about 3 weight percent lipase.

9. The food supplement formulation according to claim 8, wherein the concentration of fish oil is about 97.5 weight percent.

10. The food supplement formulation according to claim 8, wherein the concentration of peppermint oil is about 1 weight percent.

11. The food supplement formulation according to claim 8, wherein the concentration of lipase is about 1.5 weight percent.

12. An improved food supplement formulation, comprising:
  about 97.5 weight percent fish oil;
  about 1 weight percent peppermint oil; and
  about 1.5 weight percent lipase.

* * * * *